United States Patent [19]
Frank et al.

[11] Patent Number: 4,784,151
[45] Date of Patent: Nov. 15, 1988

[54] TUBULAR PRESSURE TRANSDUCER

[75] Inventors: Thomas P. Frank, Dublin; Wendell Thompson, Columbus, both of Ohio

[73] Assignee: Medex, Inc., Hilliard, Ohio

[21] Appl. No.: 31,758

[22] Filed: Mar. 30, 1997

[51] Int. Cl.$^4$ .............................................. A61B 5/02
[52] U.S. Cl. ................................... 128/675; 128/748; 73/730
[58] Field of Search ..................... 128/672.5, 748, 693, 128/734; 73/753.4, 725.7, 730

[56] References Cited

U.S. PATENT DOCUMENTS

| | | | |
|---|---|---|---|
| 2,976,865 | 3/1961 | Shipley | 128/675 |
| 3,149,492 | 9/1964 | Weinberg | 128/672 X |
| 3,336,807 | 8/1967 | Van Lint et al. | 73/754 |
| 3,545,275 | 12/1970 | Harrison et al. | 128/675 X |
| 3,747,410 | 7/1973 | Nissen et al. | 73/753 |
| 3,787,764 | 1/1974 | Andeen et al. | 73/754 X |
| 3,957,037 | 5/1976 | Fletcher et al. | 128/693 X |
| 4,028,276 | 6/1977 | Harden et al. | |
| 4,065,969 | 1/1978 | Dinwiddie | 73/727 |
| 4,160,448 | 7/1979 | Jackson | 128/673 |
| 4,215,698 | 8/1980 | Nuwayser | 128/734 |
| 4,380,237 | 4/1983 | Newbower | 128/734 X |
| 4,420,980 | 12/1983 | Dunemann et al. | 73/730 |
| 4,506,250 | 3/1985 | Kirby . | |
| 4,541,284 | 9/1985 | Guagliumi et al. | 73/754 X |
| 4,576,181 | 3/1986 | Wallace . | |
| 4,600,855 | 7/1986 | Strachan . | |
| 4,610,256 | 9/1986 | Wallace . | |
| 4,706,501 | 11/1987 | Atkinson et al. | 73/730 |

OTHER PUBLICATIONS

"Conductive Polymers as Fatigue-Damage Indicators", by J. W. Dally, and G. A. Panizza, *Experimental Mechanics*, 3/72, pp. 124-129.
"Conductive Rubber Pressure Transducers for Fluids Research", by I. Kavrak, *The Review of Scientific Instruments*, vol. 41, No. 5, pp. 628-631, May 1978.
"New Sensing . . . Conductive Polymer", Jan. 1984, *Sensor Review*, pp. 23, 24.
"A Load Cell System in Foot Pressure Analysis", by W. V. James, J. F. Orr, T. Huddleston, *Engineering in Medicine*, MEP Ltd., 1982, vol. ii, No. 3.

*Primary Examiner*—Max Hindenburg
*Assistant Examiner*—Angela D. Sykes
*Attorney, Agent, or Firm*—Wood, Herron & Evans

[57] ABSTRACT

In a blood pressure monitoring system, a transducer which is a conductive rubber tube having conductive terminals at each end. The terminals are connected to a circuit for detecting changes in resistance of the tube. The internal surface of the tubing is coated with a dielectric material.

6 Claims, 1 Drawing Sheet

TUBULAR PRESSURE TRANSDUCER

BACKGROUND OF THE INVENTION

This invention relates to a fluid (gas or liquid) pressure transducer, and particularly to a blood pressure transducer.

Blood pressure transducers are known. See, for example U.S. Pat. No. 4,576,181 disclosing a disposable blood pressure transducer and U.S. Pat. No. 4,610,256 disclosing a blood pressure transducer having a disposable dome. Such transducers are complicated, expensive, and somewhat difficult to set up to provide assurance of a complete debubbling, that is, complete removal of air bubbles in the system. Transducers of the type described in the patents referred to above employ a silicon chip forming a pressure sensor, an elastomeric diaphragm on which the chip is mounted, a temperature compensation circuit, a light shield because of the sensitivity of the silicon chip, and a housing mounting all of the foregoing elements in such a way that they can be connected in line with the tubing to which the patient's catheter is connected. The system, including the transducer and tubing, is filled with a saline solution that drips slowly through the catheter, the catheter being inserted into the patient's blood vessel. Thus, the pressure in the blood vessel is transmitted directly via the saline solution through the tubing to the transducer. The sensor is electrically connected to a blood pressure monitor presenting a visual display of the patient's blood pressure.

Less complex in structure is a tubular sensor of U.S. Pat. No. 4,600,855. That system, however, requires a special tube and piezoelectric film surrounding the tube. A complex electric circuit is employed to energize the piezoelectric film to cause the tube to resonate and to monitor the frequencies of resonance.

SUMMARY OF THE INVENTION

An objective of the present invention has been to provide a disposable pressure transducer which is exceedingly simple in its construction, is very inexpensive, and presents virtually no debubbling set up problems.

The objective is attained by providing an elastomeric tube doped with conductive particles so that its resistance changes with changes in pressure. The tube section has conductive terminals intimately connected with it at each end. The tube is inserted, as a transducer, in the fluid pressure system to be monitored. The conductive terminals are connected to the monitoring system, preferably through a bridge circuit, the tube forming one part of a Wheatstone bridge.

It has been found that such a tubular transducer, for example, carbon-doped silicon rubber, provides an excellent monitor of the pressure variations within the fluid system.

When used as a blood pressure transducer, as contrasted to an industrial application, the internal surface of the tube must be coated with a dielectric in order to insulate the electrical portion of the total system from the patient. In addition to being a satisfactory dielectric, the coating must also be biocompatible with the fluid system to which the patient is connected.

Obviously, the straight tubular section in series with the tube connected to the patient's catheter introduces no problem of debubbling. Thus, bubbles which could damp the electrical signals are eliminated as well as any hazardous bubbles that might enter the patient's circulatory system and cause embolism.

BRIEF DESCRIPTION OF THE DRAWINGS

The several features of the invention will become more readily apparent from the following detailed description taken in conjunction with the accompanying drawings in which.

DESCRIPTION OF THE PREFERRED EMBODIMENTS

Figure 1:
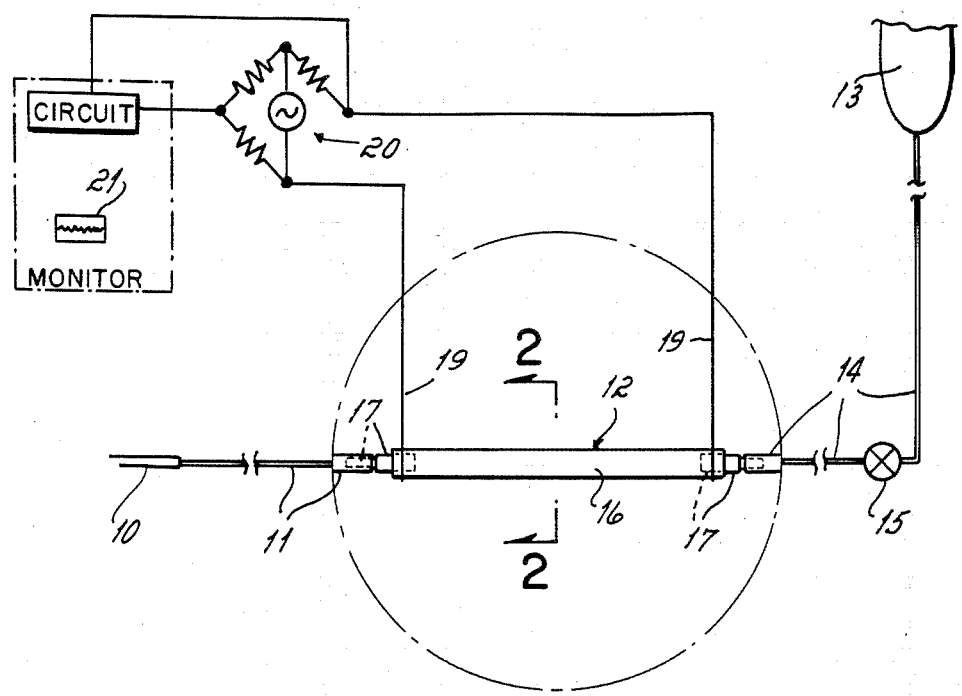
FIG. 1 is a diagrammatic view of the pressure monitoring system, the encircled portion being greatly enlarged for illustrative purposes.
Figure 2:
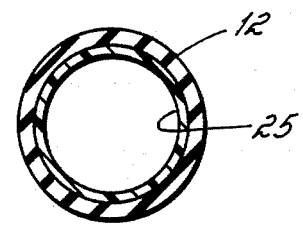
FIG. 2 is a cross section taken along lines 2—2 of FIG. 1.

Referring to FIG. 1, a conventional blood pressure monitoring system is shown. It includes a catheter 10 for insertion into a patient's blood vessel. Pressure tubing 11 connects the catheter to a transducer 12 of the present invention. A bag of saline solution 13 is connected by a tubing 14 and a flush valve 15 to the transducer.

The transducer is a tubular section or tube 16 of an elastomer that has been doped with conductive particles in such a way that its resistance changes in response to pressure applied to it. The tube has, at each end, spigot-type Luer adapters 17. Each adapter has one portion inserted into the end of the tube 16 with the remaining portion projecting from the end of the tubing and adapted to be inserted into the catheter system tubing to make a liquid-tight connection therewith.

Between the ends of the tubular section 12, two conductive terminals 19 are fastened to the exterior surface of the tube. The contact can simply be a surface contact as by wrapping a wire around the circumference of the tubular section. Those conductors are connected to the Wheatstone bridge 20. The transducer is a variable resistance element which is connected via a bridge 20 to a monitor circuit. The bridge and monitor circuit convert the changes in resistance to a visual display indicated at 21. Except for the specific transducer, all of the other elements of the circuit are conventional.

The tubing is preferably a carbon-doped silicon rubber. It has an internal coating indicated at 25. The coating could be deposited on the interior of the tubing or, alternatively, could be laminated to it by of a co-extrusion process. It is important that the internal coating provide sufficient dielectric protection to provide leakage current protection and defibrillator withstand. It also must be biocompatible with the fluids passing through it so as to avoid contamination of the patient. It must be able to withstand sterilization processes.

It has been found that a short length of tubing which is about 0.250 inch outside diameter, 0.200 in inside diameter and about $2\frac{1}{2}$ inches between conductors provides a good response from the variations in blood pressure normally found in a patient. The spacing between the conductors can be increased or decreased in order to increase or decrease the resistance between them as required for the particular application. The tubing dimensions, durometer, material resistivity can also be varied.

In operation, the variations in blood pressure that are transmitted to the interior of the tubular section 12 cause a pressure to be applied to the tubular section and this alters its resistance. The variations in resistance cause the output from the Wheatstone bridge to vary, thus providing the visual display of the patient's blood pressure.

With suitable modifications, the device is useful with industrial applications.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. Apparatus for measuring fluid pressure comprising:
   a tube adapted to contain fluid whose pressure is to be measured,
   one section of said tube being a conductive elastomer,
   spaced conductive terminals in electrical contact with said section,
   and means for measuring changes in the resistance of said section between said conductive terminals as the pressure of the fluid in said tube changes.

2. A transducer for measuring fluid pressure comprising:
   a tube of conductive rubber,
   electrodes secured to opposite end portions of said tube,
   means for connecting said tube to the fluid system whose pressure is to be measured, and means for measuring changes in the resistance of the tube between said electrodes as the pressure of the fluid system changes.

3. A transducer as in claim 2 in which said tube is a carbon-doped silicon rubber.

4. A transducer as in claim 2 in which said connecting means comprises:
   a Luer fitting inserted into each end of said tube.

5. A transducer as in claim 2 further comprising a dielectric coating on the internal surface of said tubing.

6. Blood pressure measuring apparatus comprising:
   a catheter for insertion into a patient's blood vessel,
   tubing connected to said catheter,
   a tube transducer connected to said tubing including a conductive elastomer tube having conductive terminals connected to each end and a biocompatible dielectric coating on the internal surface of said tube,
   means for supplying a saline solution to said catheter, tubing and transducer,
   and monitor means connected to said conductive terminals.

* * * * *

UNITED STATES PATENT AND TRADEMARK OFFICE
CERTIFICATE OF CORRECTION

PATENT NO. : 4,784,151
DATED : November 15, 1988
INVENTOR(S) : Thomas P. Frank and Wendell Thompson It is certified that error appears in the above-identified patent and that said Letters Patent is hereby corrected as shown below:

```
    On the title page
 " [22] Filed:   Mar. 30, 1997" should be
 -- [22] Filed:  Mar. 30, 1987 --.
```

Signed and Sealed this

Twenty-eighth Day of March, 1989

Attest:

DONALD J. QUIGG

*Attesting Officer*    *Commissioner of Patents and Trademarks*